United States Patent
Guerra et al.

(10) Patent No.: US 12,428,384 B2
(45) Date of Patent: Sep. 30, 2025

(54) HYDROXY-FUNCTIONALIZED TRIAZINE COMPOUNDS, CURABLE FLUOROPOLYMER COMPOSITIONS COMPRISING SUCH COMPOUNDS AND CURED ARTICLES THEREFROM

(71) Applicant: 3M INNOVATIVE PROPERTIES COMPANY, St. Paul, MN (US)

(72) Inventors: Miguel A. Guerra, Woodbury, MN (US); Tatsuo Fukushi, Woodbury, MN (US); Michael H. Mitchell, Edina, MN (US); Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 946 days.

(21) Appl. No.: 17/615,127

(22) PCT Filed: Jun. 22, 2020

(86) PCT No.: PCT/IB2020/055859
§ 371 (c)(1),
(2) Date: Nov. 30, 2021

(87) PCT Pub. No.: WO2020/261088
PCT Pub. Date: Dec. 30, 2020

(65) Prior Publication Data
US 2022/0227718 A1    Jul. 21, 2022

Related U.S. Application Data

(60) Provisional application No. 62/868,032, filed on Jun. 28, 2019.

(51) Int. Cl.
*C07D 251/24* (2006.01)
(52) U.S. Cl.
CPC .................. *C07D 251/24* (2013.01)
(58) Field of Classification Search
CPC .................................................. C07D 251/24
See application file for complete search history.

(56) References Cited

U.S. PATENT DOCUMENTS

| | | | |
|---|---|---|---|
| 4,233,421 A | 11/1980 | Worm | |
| 4,912,171 A | 3/1990 | Grootaert | |
| 5,086,123 A | 2/1992 | Guenthner | |
| 5,262,490 A | 11/1993 | Kolb | |
| 5,591,804 A | 1/1997 | Coggio | |
| 5,852,133 A | 12/1998 | Gupta et al. | |
| 5,891,965 A | 4/1999 | Worm | |
| 5,929,169 A | 7/1999 | Jing | |
| 2002/0183458 A1 | 12/2002 | Grootaert et al. | |
| 2004/0116742 A1 | 6/2004 | Guerra | |
| 2005/0143529 A1 | 6/2005 | Grootaert | |
| 2006/0135827 A1 | 6/2006 | Grootaert et al. | |
| 2008/0035883 A1 | 2/2008 | Andreevich et al. | |
| 2016/0369021 A1 | 12/2016 | Manzoni et al. | |
| 2018/0044473 A1 | 2/2018 | Palmese et al. | |

FOREIGN PATENT DOCUMENTS

| | | |
|---|---|---|
| CN | 105358591 A | 2/2016 |
| GB | 1350806 A | 4/1974 |
| JP | H06-340710 | 12/1994 |
| JP | H-10237130 A | 9/1998 |
| WO | WO 1997-005122 | 2/1997 |
| WO | WO 2012-072532 | 6/2012 |

OTHER PUBLICATIONS

Tumanova, "Reaction of perfluoromethyl perfluorovinyl ether and nucleophiles", Database Chemabs [Online] Chemical Abstracts Service. Columbus. Ohio, US, XP002800087, Database accession No. 1965.74219, Apr. 22, 2001, 1 page.

International Search Report for PCT International Application No. PCT/IB2020/055859, mailed on Sep. 8, 2020, 5 pages.

*Primary Examiner* — Paul V Ward
(74) *Attorney, Agent, or Firm* — Julie Lapos-Kuchar

(57) ABSTRACT

Described herein are compounds according to Formula (I) wherein each Rf is independently selected from a perfluorinated divalent group comprising 2 to 12 carbon atoms; and m is an integer independently selected from 1 to 3. A method of making the compound from a hydroxy-containing vinyl ether and excess ammonia is disclosed. In one embodiment, the hydroxy-functionalized triazine compound is used in a curable fluoropolymer composition and cured to form articles.

(I)

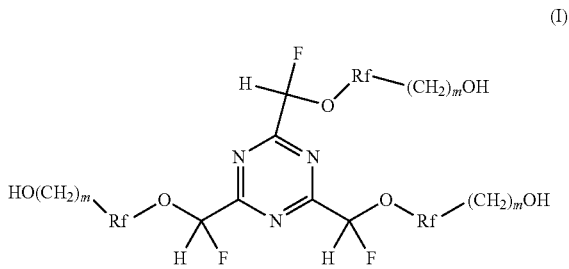

19 Claims, No Drawings

HYDROXY-FUNCTIONALIZED TRIAZINE COMPOUNDS, CURABLE FLUOROPOLYMER COMPOSITIONS COMPRISING SUCH COMPOUNDS AND CURED ARTICLES THEREFROM

TECHNICAL FIELD

A hydroxy-functionalized triazine compound is described along with a method of making such a compound. Also described are curable fluoropolymer compositions comprising such compounds and cured articles therefrom.

SUMMARY

There is a continuing desire to develop novel curing systems for fluoropolymers, which are more cost effective, have a higher efficiency of cure, and/or have improved properties/performance.

In one aspect, a novel compound is described as shown in Formula (I)

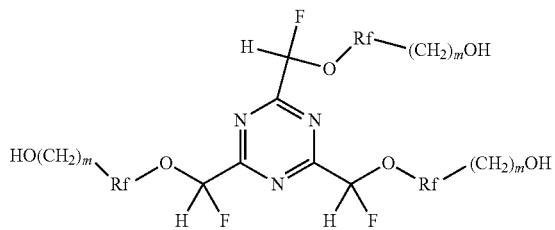

wherein each Rf is independently selected from a perfluorinated divalent group comprising 2 to 12 carbon atoms; and m is an integer independently selected from 1 to 3.

In another aspect, a method of making the compound according to Formula (I) is described, the method comprising:
reacting a vinyl ether monomer according to Formula (II), with ammonia to form an amidine molecule; and heating the amidine molecule to form the compound according to Formula (I), where Formula (II) is

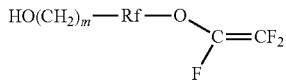

wherein Rf is a perfluorinated divalent group comprising 2 to 12 carbon atoms; and m is an integer independently selected from 1 to 3.

In yet another aspect, a curable composition is described comprising (a) an amorphous fluorinated polymer capable of being dehydrofluorinated, and (b) the compound according to Formula I.

In one aspect, the curable composition from above is cured to form an article such as an o-ring, a seal, a gasket, a hose, or a sheet.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and "and/or" is used to indicate one or both stated cases may occur, for example A and/or B includes, (A and B) and (A or B);

"backbone" refers to the main continuous chain of the polymer;

"crosslinking" refers to connecting two pre-formed polymer chains using chemical bonds or chemical groups;

"cure site" refers to functional groups, which may participate in crosslinking;

"interpolymerized" refers to monomers that are polymerized together to form a polymer backbone;

"monomer" is a molecule which can undergo polymerization which then form part of the essential structure of a polymer;

"perfluorinated" means a group or a compound derived from a hydrocarbon wherein all hydrogen atoms have been replaced by fluorine atoms. A perfluorinated compound may however still contain other atoms than fluorine and carbon atoms, like oxygen atoms, chlorine atoms, bromine atoms and iodine atoms; and "polymer" refers to a macrostructure having a number average molecular weight (Mn) of at least 30,000 dalton, at least 50,000 dalton, at least 100,000 dalton, at least 300,000 dalton, at least 500,000 dalton, at least, 750,000 dalton, at least 1,000,000 dalton, or even at least 1,500,000 dalton and not such a high molecular weight as to cause premature gelling of the polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

The present disclosure is directed toward a compound according to formula I. Along with a method of making such compound as well as their use curable fluoropolymer compositions.

Hydroxy-Functionalized Triazine Compound

The hydroxy-functionalized triazine compounds of the present disclosure are according to Formula (I):

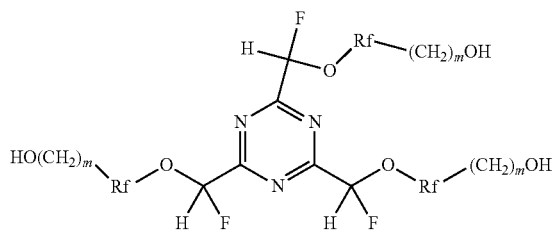

wherein each Rf is independently selected from a perfluorinated divalent group comprising 2 to 12 carbon atoms; and m is an integer independently selected from 1, 2, or 3.

It is to be appreciated that in the present disclosure, irrespective of what is depicted in any of the chemical structures, no representations are made regarding the stereoisomerism of the compounds and their spatial arrangement of atoms.

Rf is a divalent perfluorinated group comprising 2 to 12 carbon atoms. In one embodiment Rf comprises at least 2, 3, 4, 5, 6, or even 8 carbon atoms. In one embodiment Rf comprises at most 6, 8, 10 or even 12 carbon atoms. Rf may be linear, branched, and/or cyclic in nature. In one embodiment, Rf is linear alkylene, such as —$(CF_2)_n$—, where n is an integer of at least 2, 3, or even 4; and at most 5, 6, 7, or even 8. In one embodiment, Rf is a branched alkylene such as —$[(CF_2CF(CF_3)]_n$—, where n is an integer of at least 2, 3, 4; and at most 5, 6, 7, or even 8.

Rf may optionally contain at least one catenated oxygen (i.e., ether) and/or nitrogen (i.e., amine) atom. For example, Rf may comprise —$(CF_2)_p$—O—$(CF_2)_q$—, —$(OCF_2CF_2)_q$—, —$(OCF_2CF(CF_3))_p$— and/or —$(CF_2CF(CF_3))_p$—O—$(CF_2)_q$—, wherein p is an integer of 1, 2, 3, 4, 5, 6, 7, 8, 9, 10 or 11 and q is an integer from 1, 2, 3, 4, 5, 6, 7, 8, 9, 10 or 11, such that the sum of p+q is 2, 3, 4, 5, 6, 7, 8, 9, 10, 11, or 12.

The Rf groups may or may not be same, however, it is preferable that the three Rf groups in Formula (I) are identical.

The compound according to Formula I are small molecules, having a molecular weight of at least 600 g/mole and less than 5000, 4000, 3000, 2500, 2200, 2000, 1800, 1500, 1200, or even 1000 grams/mole.

Exemplary compounds of Formula (I) include:
$[HOCH_2(CF_2)_2OCFH]_3$—$C_3N_3$, $[HO(CH_2)_2(CF_2)_2OCFH]_3$—$C_3N_3$,
$[HO(CH_2)_3(CF_2)_2OCFH]_3$—$C_3N_3$, $[HO(CH_2)(CF_2)_3OCFH]_3$—$C_3N_3$, $[HO(CH_2)(CF_2)_4OCFH]_3$—$C_3N_3$, $[HO(CH_2)(CF_2)_5OCFH]_3$—$C_3N_3$,
$[HO(CH_2)(CF_2)_6OCFH]_3$—$C_3N_3$, $[HO(CH_2)(CF_2)_6OCFH]_2$—$C_3N_3$—$[CHFO(CF_2)_2(CH_2)OH]$,
$[HO(CH_2)(CF(CF_3)O(CF_2)_6OCFH]_2$—$C_3N_3$—$[CHFO(CF_2)_2OCF(CF_3)CH_2OH]$,
$[HOCH_2CH_2CF(CF_3)O(CF_2)_2OCFH]_3$—$C_3N_3$,
$[HOCH_2CF(CF_3)O(CF_2)_2OCFH]_3$—$C_3N_3$,
$[HOCH_2(CF_2)_3OCF(CF_3)CF_2OCFH]_3$—$C_3N_3$,
$[HOCH_2CH_2(CF_2)_4OCFH]_3$—$C_3N_3$,
$[HOCH_2(CF_2)_2OCF(CF_3)CF_2OCFH]_3$—$C_3N_3$,
$[HOCH_2CH_2(CF_2)_2OCF_2CF(CF_3)OCFH]_3$—$C_3N_3$, and
$[HOCH_2(CF_2)_5OCF(CF_3)CF_2OCFH]_3$—$C_3N_3$,
where $C_3N_3$ represents the triazine ring.

Method of Making

The compounds according to Formula (I) may be made by reacting a hydroxy alkylene perfluorovinyl ether with excess ammonia to produce a hydroxy alkylene hydrofluoroether amidine. This reaction may be done directly or can be done in multiple steps by first isolating the hydroxy alkylene hydrofluoroether nitrile intermediate and adding additional ammonia to make the corresponding hydroxy alkylene hydrofluoroether amidine. These hydroxy alkylene hydrofluoroether amidines can then be heated to isolate the trifunctional hydrofluoroether triazines.

The multi-step reaction to make the compound according to Formula (I) are shown below:
$HO(CH_2)_m$—Rf—O—CF=$CF_2$+$3NH_3$→$HO(CH_2)_m$—Rf—O—CHF—C≡N+$2HF·NH_3$
$HO(CH_2)_m$—Rf—O—CHF—CN+$NH_3$→$HO(CH_2)_m$—Rf—O—CHF—C(=NH)$NH_2$
$3[HO(CH_2)_m$—Rf—O—CHF—C(=NH)$NH_2]$+heat→Formula (I)+$3NH_3$
where Rf and m are the same as defined above.

In the above proposed reaction scheme, 1 mole of vinyl ether monomer of Formula (II) is reacted with three equivalents of ammonia to form a nitrile molecule of Formula (III). The amidine molecule of Formula (IV) can be derived by adding another mole of ammonia to the nitrile molecule of Formula (III) or adding excess ammonia to Formula (II) to isolate the amidine molecule directly. The amidine molecule of Formula (IV) can then be heated to arrive at the compound according to Formula (I). The formed nitrile molecule of Formula (III) can also be directly cyclized to form the compound of Formula (I) under heat, which can be accelerated, for example, in the presence of a catalytic amount of ammonia.

The vinyl ether monomer is of the structure according to Formula (II):

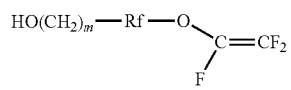

wherein Rf is a perfluorinated divalent group as described above; and m is 1, 2, or 3.

Exemplary vinyl ether monomers according to Formula (II) include:
$HOCH_2(CF_2)_3OCF=CF_2$, $HOCH_2(CF_2)_5O\ CF=CF_2$,
$HOCH_2(CF_2)_3OCF(CF_3)CF_2O\ CF=CF_2$, $HOCH_2CH_2(CF_2)_4OCF=CF_2$,
$HOCH_2(CF_2)_2OCF(CF_3)CF_2O\ CF=CF_2$, $HOCH_2CH_2(CF_2)_2OCF(CF_3)CF_2OCF=CF_2$, and
$HOCH_2(CF_2)_5OCF(CF_3)CF_2O\ CF=CF_2$.

In the first step of the reaction disclosed herein, the vinyl ether monomer according to Formula (II) is reacted with a controlled amount (for example 3 moles of ammonia per mole of vinyl ether monomer) of ammonia ($NH_3$) to form the corresponding nitrile molecule, $HO(CH_2)_m$ Rf—O—CHF—CN (III), wherein Rf and m are described above.

Exemplary nitrile molecules according to Formula (III) include:
$HOCH_2(CF_2)_3OCFHCN$, $HOCH_2(CF_2)_5OCFHCN$, $HOCH_2(CF_2)_3OCF(CF_3)CF_2OCFHCN$ $HOCH_2CH_2(CF_2)_4OCFHCN$, $HOCH_2(CF_2)_2OCF(CF_3)CF_2OCFHCN$, $HOCH_2CH_2(CF_2)_2OCF(CF_3)CF_2OCFHCN$, and $HOCH_2(CF_2)_5\ OCF(CF_3)CF_2OCFHCN$.

In the second step of the reaction, the corresponding nitrile molecule is reacted with an additional mole of ammonia to form the amidine molecule,
$HO(CH_2)_m$—Rf—O—CFH—C(=NH)$NH_2$(IV), in the presence of an excess amount of ammonia,
wherein Rf and m are described above.

Exemplary amidine molecules according to Formula (IV) include:
$HOCH_2(CF_2)_3OCFHC(=NH)NH_2$, $HOCH_2(CF_2)_5OCFHC(=NH)NH_2$,
$HOCH_2(CF_2)_3OCF(CF_3)CF_2OCFHC(=NH)NH_2$,
$HOCH_2CH_2(CF_2)_4OCFHC(=NH)NH_2$,
$HO(CH_2)_3(CF_2)_4OCFHC(=NH)NH_2$, $HOCH_2(CF_2)_2OCF(CF_3)CF_2OCFHC(=NH)NH_2$,
$HOCH_2CH_2(CF_2)_2OCF(CF_3)CF_2OCFHC(=NH)NH_2$, and
$HOCH_2(CF_2)_5OCF(CF_3)CF_2OCFHC(=NH)NH_2$.

The amidine molecule is then heated to temperature of at least 100° C., 120° C., or even 140° C. and, in some embodiments, at most 200° C., for cyclization of the amidine molecules to form the compound according to Formula (I) along with ammonia.

In the above reaction schemes, typically, a solvent is used to aid the reaction even though the reactions may be done in the absence of a solvent. Preferably, the selected solvent is a polar aprotic solvent, which has some solubility to the reactants to enable a fast reaction. Preferably, the used solvent is anhydrous in order to eliminate the hydrolysis side reaction of nitrile. Solvents that can be used, but not limited to are 1,4-dioxane, methyl-t-butyl ether, monoglyme, diglyme, triglyme, tetrahydrofuran, N-methyl pyrrolidone, N,N-dimethyl formamide, sulfolane, and acetonitrile. Methyl-t-butyl ether is the preferred solvent.

Addition of ammonia to the vinyl ether monomer to form the nitrile and/or amidine molecules can be done from −35° C. to 50° C. Preferably from −10° C. to 25° C. and more preferably from −5° C. to 10° C. Pressure in the reaction can range from 0 psi (pounds per square inch) to 100 psi, preferably from 10 psi to 75 psi and more preferably form 15 psi to 50 psi. The ratio of ammonia to the vinyl ether monomer to form the amidine molecule according to Formula (IV) can be from at least 3, 4, 5, 6, or even 7 moles of ammonia to 1 mole vinyl ether monomer. In one embodiment, the ratio of ammonia to the vinyl ether monomer of Formula (II) to form the amidine molecule according to Formula (IV) is no more than 8, or even 10 moles of ammonia to 1 mole of the vinyl ether monomer.

Depending on the reaction product desired, the desired reaction product can be isolated using techniques known in the art. For example, isolation of the nitrile molecule can be done by first filtration of the ammonium fluoride salt, removing the solvent by distillation or rotary evaporation and final distillation to isolate the nitrile molecule. A similar procedure is followed when isolating the amidine molecule, except the amidine molecule is not distilled. In one embodiment, the resulting triazine-containing compound according to Formula (I) is in a purified form, which means the compound according to Formula (I) is at least 75, 80, 85, 90, 95, 98, or even 99 wt % pure.

The reaction described above, is a straightforward reaction to produce hydroxy functionalized hydrofluoroether triazines. For example, dihydroalcohol perfluoropentyl vinyl ether, $HOCH_2(CF_2)_5OCF=CF_2$, which can be reacted with excess ammonia in methyl t-butyl ether solvent in a Parr reactor to isolate $HOCH_2(CF_2)_5OCFHC(=NH)NH_2$ then heated to 140° C. to make $[HOCH_2(CF_2)_5OCFH]_3-C_3N_3$, a trihydroxy functional hydrofluoroether triazine.

The compounds according to Formula (I) may be used as a crosslinking agent in the curing of amorphous fluorinated polymers.

Curable Composition:

In one embodiment of the present disclosure, the compound according to Formula (I) is combined with an amorphous partially fluorinated polymer capable of being dehydrofluorinated to form a fluoroelastomer.

The amorphous partially fluorinated polymer capable of being dehydrofluorinated is a polymer comprising carbon-carbon double bonds and/or is capable of forming carbon-carbon double bonds along the polymer chain under desired curing conditions.

The amorphous partially fluorinated polymer is a polymer comprising at least one carbon-hydrogen bond adjacent to a carbon-fluorine bond on the backbone of the polymer. In one embodiment, the amorphous partially fluorinated polymer is highly fluorinated, wherein at least 60, 70, 80, or even 90% of the polymer backbone comprises C—F bonds.

The amorphous partially fluorinated polymer of the present disclosure comprises carbon-carbon double bonds and/or is capable of forming carbon-carbon double bonds along the polymer chain. In one embodiment, the amorphous partially fluorinated fluoropolymer comprises carbon-carbon double bonds along the backbone of the partially fluorinated amorphous fluoropolymer or is capable of forming carbon-carbon double bonds along the backbone of the partially fluorinated amorphous fluoropolymer. In another embodiment, the amorphous partially fluorinated fluoropolymer comprises carbon-carbon double bonds or is capable of forming carbon-carbon double bonds in a pendent group off of the backbone of the partially fluorinated amorphous fluoropolymer.

The fluoropolymer capable of forming carbon-carbon double bonds means that the fluoropolymer contains units capable of forming double bonds. Such units include, for example, two adjacent carbons along the polymer backbone or pendent side chain, wherein a hydrogen is attached to the first carbon and a leaving group is attached to the second carbon. During an elimination reaction (e.g., thermal reaction, and/or use of acids or bases), the leaving group and the hydrogen leave forming a double bond between the two carbon atoms. An exemplary leaving group includes: a halide, an alkoxide, a hydroxide, a tosylate, a mesylate, an amine, an ammonium, a sulfide, a sulfonium, a sulfoxide, a sulfone, and combinations thereof. Also contemplated would be a fluoropolymer comprising adjacent carbons either having both bromine or both iodine atoms attached resulting in the leaving of $Br_2$ or $I_2$.

The amorphous partially fluorinated polymer comprises a plurality of these groups (carbon-carbon double bonds or groups capable of forming double bonds) to result in a sufficient cure. Generally, this means at least 0.1, 0.5, 1, 2, or even 5 mol % at most 7, 10, 15, or even 20 mol % (i.e., moles of these carbon-carbon double bonds or precursors thereof per mole of polymer).

In one embodiment, the amorphous partially fluorinated polymer is derived from at least one hydrogen containing monomer such as vinylidene fluoride.

In one embodiment, the amorphous partially fluorinated polymer comprises adjacent copolymerized units of vinylidene fluoride (VDF) and hexafluoropropylene (HFP); copolymerized units of VDF (or tetrafluoroethylene) and a fluorinated comonomer capable of delivering an acidic hydrogen atom to the polymer backbone, such as trifluoroethylene; vinyl fluoride; 3,3,3-trifluoropropene-1; pentafluoropropene (e.g., 2-hydropentafluoropropylene and 1-hydropentafluoropropylene); 2,3,3,3-tetrafluoropropene; and combinations thereof.

In some embodiments, small amounts (e.g., less than 10, 5, 2, or even 1 wt %) of additional monomers may be used to derive the amorphous partially fluorinated polymer so long as the fluorinated polymer is able to be cured with the compound of Formula (I) as disclosed herein, and optionally with a polyhydroxy curative.

In one embodiment, the amorphous partially fluorinated polymer is additionally derived from a hydrogen containing monomer including: pentafluoropropylene (e.g., 2-hydropentafluropropylene), propylene, ethylene, isobutylene, and combinations thereof.

In one embodiment, the amorphous partially fluorinated polymer is additionally derived from a perfluorinated monomer. Exemplary perfluorinated monomers include: hexafluoropropene; tetrafluoroethylene; chlorotrifluoroethylene; perfluoro ether monomers, and combinations thereof.

Exemplary perfluoro ether monomers are of the Formula (III)

$$CF_2=CF(CF_2)_bO(R_{f'}O)_n(R_{f'}O)_mR_f \qquad (III)$$

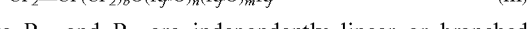

where $R_{f'}$ and $R_{f'}$ are independently linear or branched perfluoroalkylene radical groups comprising 2, 3, 4, 5, or 6 carbon atoms, m and n are independently an integer selected from 0, 1, 2, 3, 4, 5, 6, 7, 8, 9, and 10, and $R_f$ is a perfluoroalkyl group comprising 1, 2, 3, 4, 5, or 6 carbon atoms. Exemplary perfluoroalkyl vinyl ether monomers include: perfluoro (methyl vinyl) ether (PMVE), perfluoro (ethyl vinyl) ether (PEVE), perfluoro (n-propyl vinyl) ether (PPVE-1), perfluoro-2-propoxypropylvinyl ether (PPVE-2), perfluoro-3-methoxy-n-propylvinyl ether, perfluoro-2-methoxy-ethylvinyl ether, perfluoro-methoxy-methylvinylether ($CF_3$—O—$CF_2$—O—CF=$CF_2$), and $CF_3$—$(CF_2)_2$—O—CF($CF_3$)—$CF_2$—O—CF($CF_3$)—$CF_2$—O—CF=$CF_2$. Exemplary perfluoroalkyl allyl ether monomers include: perfluoro (methyl allyl) ether ($CF_2$=CF—$CF_2$—O—$CF_3$), perfluoro (ethyl allyl) ether, perfluoro (n-propyl allyl) ether, perfluoro-2-propoxypropyl allyl ether, perfluoro-3-methoxy-n-propylallyl ether, perfluoro-2-methoxy-ethyl allyl ether, perfluoro-methoxy-methyl allyl ether, and $CF_3$—$(CF_2)_2$—O—CF($CF_3$)—$CF_2$—O—CF($CF_3$)—$CF_2$—O—$CF_2$CF=$CF_2$.

Exemplary types of amorphous partially fluorinated polymers include those comprising interpolymerized units derived from (i) vinylidene fluoride, tetrafluoroethylene, and propylene; (ii) vinylidene fluoride with hexafluoropropylene; (iii) hexafluoropropylene, tetrafluoroethylene, and vinylidene fluoride; (iv) hexafluoropropylene and vinylidene fluoride, (v) tetrafluoroethylene, propylene, and 3,3,3-trifluoropropene; (vi) tetrafluoroethylene, and propylene; and (vii) blends thereof.

In one embodiment of the present disclosure, the amorphous partially fluorinated polymer is cured with the compound according to Formula (I) and is substantially free (having less than 0.05, less than 0.01, less than 0.05 wt % or even none relative to the amorphous partially fluorinated polymer) of a traditional curative (such as peroxide, and/or polyhydroxy curing agent). Typically, at least 0.05, 0.1, 1, 2, 3, or even 4 parts; and at most 5, 10, 15, 20, or even 25 parts by weight of the compound according to Formula (I) is used per 100 parts by weight of amorphous partially fluorinated polymer. The extent of the cure and performance can be evaluated by cure rheology, hardness, tensile properties (such as tensile at break, elongation at break, tensile at 50% elongation, and/or tensile at 100% elongation), and/or compression set.

In another embodiment of the present disclosure, the composition comprises a dehydrofluorinating agent. Exemplary dehydrofluorinating agents include organoonium compounds, such as quaternary ammonium hydroxides or salts, quaternary phosphonium hydroxides or salts, and ternary sulfonium hydroxides or salts.

Briefly, a phosphonium and ammonium salts or compounds comprise a central atom of phosphorous or nitrogen, respectively, covalently bonded to four organic moieties by means of a carbon-phosphorous (or carbon-nitrogen) covalent bonds and is ionically associated with an anion. The organic moieties can be the same or different.

Briefly, a sulfonium compound is a sulfur-containing organic compound in which at least one sulfur atom is covalently bonded to three organic moieties having from 1 to 20 carbon atoms by means of carbon-sulfur covalent bonds and is ionically associated with an anion. The organic moieties can be the same or different. The sulfonium compounds may have more than one relatively positive sulfur atom, e.g. $[(C_6H_5)_2S^+(CH_2)_4S^+(C_6H_5)_2]_2Cl^-$, and two of the carbon-sulfur covalent bonds may be between the carbon atoms of a divalent organic moiety, i.e., the sulfur atom may be a heteroaton in a cyclic structure.

Organo-onium compounds are known in the art, such as in U.S. Pat. No. 4,233,421 (Worm), U.S. Pat. No. 4,912,171 (Grootaert et al.), U.S. Pat. No. 5,086,123(Guenthner et al.), and U.S. Pat. No. 5,262,490(Kolb et al.), and U.S. Pat. No. 5,929,169, all of whose descriptions are herein incorporated by reference. Another class of useful organo-onium compounds include those having one or more pendent fluorinated alkyl groups. Generally, the most useful fluorinated onium compounds are disclosed in U.S. Pat. No. 5,591,804 (Coggio, et al.).

Exemplary organoonium compounds include: $C_3$-$C_6$ symmetrical tetraalkylammonium salts, unsymmetrical tetraalkylammonium salts wherein the sum of alkyl carbons is between 8 and 24 and benzyltrialkylammonium salts wherein the sum of alkyl carbons is between 7 and 19(for example tetrabutylammonium bromide, tetrabutylammonium chloride, benzyltributylammonium chloride, benzyltriethylammonium chloride, tetrabutylammonium hydrogen sulfate and tetrabutylammonium hydroxide, phenyltrimethylammonium chloride, tetrapentylammonium chloride, tetrapropylammonium bromide, tetrahexylammonium chloride, and tetrapentylammonium bromidetetramethylammonium chloride); quaternary phosphonium salts, such as tetrabutylphosphonium salts, tetraphenylphosphonium chloride, benzyltriphenylphosphonium chloride, tributylallylphosphonium chloride, tributylbenzyl phosphonium chloride, tributyl-2-methoxypropylphosphonium chloride, benzyldiphenyl(dimethylamino)phosphonium chloride, 8-benzyl-1,8-diazobicyclo[5.4.0]7-undecenium chloride, benzyltris(dimethylamino)phosphonium chloride, and bis(benzyldiphenylphosphine)iminium chloride. Other suitable organoonium compounds include 1,8-diazabicyclo[5.4.0]undec-7-ene and 1,5-diazabicyclo[4.3.0]non-5-ene. Phenolate is a preferred anion for the quaternary ammonium and phosphonium salts.

In one embodiment, the organoonium compound is used from at least 1, 1.5, 2, or even 2.5 millimoles and at most 3.5, 4, 4.5 or even 5 millimoles per 100 parts (by weight in grams) of the amorphous partially fluorinated polymer.

In one embodiment, the curable composition comprises an organic or inorganic base. Exemplary bases include $Ca(OH)_2$, 1,8-diazabicyclo[5,4,0]undec-7-ene (DBU), triethylamine, and tributyl amine. 1,8-diazabicyclo(5.4.0)undec-7-ene salt (DBU salt), a 1,5-diazabicyclo(4.3.0)-non-5-ene salt (DBN salt), and 1,5-diazabicyclo(4.3.0)-non-5-ene (DBN).

In one embodiment, the amorphous partially fluorinated polymer in curable composition, should be substantially free of iodine, bromine, and/or nitrile cure sites, meaning that the fluorinated polymer comprises less than 0.1, 0.05, 0.01, or even 0.005 wt % or even no I, Br, and C≡N versus the weight of the amorphous partially fluorinated polymer.

The curable compositions can also contain a wide variety of additives of the type normally used in the preparation of elastomeric compositions, such as acid acceptors, process aides, pigments, fillers, pore-forming agents, and those known in the art.

Such fillers include: an organic or inorganic filler such as clay, silica ($SiO_2$), alumina, iron red, talc, diatomaceous earth, barium sulfate, wollastonite ($CaSiO_3$), calcium carbonate ($CaCO_3$), calcium fluoride, titanium oxide, iron oxide and carbon black fillers, a polytetrafluoroethylene powder, PFA (TFE/perfluorovinyl ether copolymer) powder, an electrically conductive filler, a heat-dissipating filler, and the like may be added as an optional component to the composition. Those skilled in the art are capable of selecting specific fillers at required amounts to achieve desired physical characteristics in the cured product. The filler components may result in a cured product that is capable of retaining a preferred elasticity and physical tensile, as indicated by an elongation and tensile strength value, while retaining desired properties such as retraction at lower temperature (TR-10).

In one embodiment, the curable composition and/or cured product comprises less than 40, 30, 20, 15, or even 10% by weight of the filler.

Conventional adjuvants may also be incorporated into the curable composition of the present disclosure to enhance the properties in the resulting cured product. For example, acid acceptors may be employed to facilitate the cure and thermal stability of the compound. Suitable acid acceptors may include magnesium oxide, lead oxide, calcium oxide, calcium hydroxide, dibasic lead phosphite, zinc oxide, barium carbonate, strontium hydroxide, calcium carbonate, hydrotalcite, alkali stearates, magnesium oxalate, or combinations thereof. The acid acceptors are preferably used in amounts ranging from at least 1, 2, 4, or even 5%; and at most 10, 15, or even 20% weight per weight of the fluorinated polymer.

In one embodiment, the curable compositions (and the resulting cured articles) are substantially free of inorganic acid acceptors, meaning that the curable composition (or resulting cured article) contains less than 0.5, 0.1, 0.05, 0.01% be weight per weight of the fluorinated polymer, or even no inorganic acid acceptor.

In one embodiment, the curable composition comprises a fluoroaliphatic sulfonamide. Such compounds can be used to improve the cure. Exemplary a fluoroaliphatic sulfonamides include $C_4F_4SO_2NHCH_3$, and $CF_3$-(arylC$_6$F$_4$)—$CF_2SO_2NHC_2H_5$ as disclosed in U.S. Pat. No. 5,500,042. Such fluoroaliphatic sulfonamides may be used in at least 0.25, 0.5, 1, 2, or even 4% and no more than 5, 8, or even 10% by weight based on the weight of the fluorinated polymer.

The curable compositions may be prepared by mixing the compound of Formula (I), the amorphous fluorinated polymer, and any additional components in conventional rubber processing equipment to provide a solid mixture, i.e. a solid polymer containing the additional ingredients, also referred to in the art as a "compound". This process of mixing the ingredients to produce such a solid polymer composition containing other ingredients is typically called "compounding". Such equipment includes rubber mills, internal mixers, such as Banbury mixers, and mixing extruders. The temperature of the mixture during mixing typically will not rise above about 120° C. During mixing the components and additives are distributed uniformly throughout the resulting amorphous fluorinated polymer "compound" or polymer sheets. The "compound" can then be extruded or pressed in a mold, e.g., a cavity or a transfer mold and subsequently be oven-cured. In an alternative embodiment, curing can be done in an autoclave.

Pressing of the compounded mixture (i.e., press cure) is typically conducted at a temperature of about 120-220° C., preferably about 140-200° C., for a period of about 1 minute to about 15 hours, usually for about 1-15 minutes. A pressure of about 700-20,000 kPa, preferably about 3400-6800 kPa, is typically used in molding the composition. The molds first may be coated with a release agent and prebaked.

The molded vulcanizate can be post cured in an oven at a temperature of about 140-240° C., preferably at a temperature of about 160-230° C., for a period of about 1-24 hours or more, depending on the cross-sectional thickness of the sample. For thick sections, the temperature during the post cure is usually raised gradually from the lower limit of the range to the desired maximum temperature. The maximum temperature used is preferably about 260° C. and is held at this value for about 1 hour or more.

The cured fluoroelastomer is particularly useful as hoses, seals, gaskets, and molded parts in automotive, chemical processing, semiconductor, aerospace, and petroleum industry applications, among others.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Millipore, Saint Louis, Missouri, or may be synthesized by conventional methods.

The following abbreviations are used in this section: g=grams, cm=centimeters, min=minutes, h=hours, ° C.=degrees Celsius, ° F.=degrees Fahrenheit, MPa= megapascals, mol=moles, wt %=weight percent, L=liters, mL=milliLiters, NMR=nuclear magnetic resonance, FTIR=Fourier transform infrared spectrophotometry, DSC=differntial scanning calorimetry, J=Joules. Abbreviations for materials used in this section, as well as descriptions of the materials, are provided in Table 1.

TABLE 1

| Abbreviation | Description and Source |
| --- | --- |
| MA3 | $CF_3CF_2CF_2OCF_2CF=CF_2$ |
| | prepared as described in U.S. Pat. No. 5,891,965 as PPAE-2 |
| MV5CH2OH | HO—CH$_2$C5F$_{10}$—O—CF=CF$_2$ |
| | prepared as described in Example 1, below |
| Ammonia | Anhydrous, Millipore-Sigma, Milwaukee, Wisconsin |
| Methyl tert-butyl ether | Millipore-Sigma |
| Perfluoroadipoyl fluoride | Exfluor Research Corp., Austin, Texas |
| Hexafluoropropylene oxide | Chemours Co., Wilmington, Delaware |
| Sodium carbonate | EMD Millipore, Darmstaadt, Germany |
| Diglyme | Millipore-Sigma |
| Sulfuric acid | EMD Millipore |
| Methanol | Fisher Scientific, Leicestershire, United Kingdom |
| Sodium borohydride | Millipore-Sigma |
| Isopropanol | VWR, Radnor, Pennsylvania |
| Fluoropolymer A | A fluoroelastomer derived from 60.6 wt % vinylidene fluoride (VDF) and 39.4 wt % hexafluoropropylene (HFP) with 65.9 wt % fluorine content and Mooney Viscosity ML1 + 10 @ 121° C. of 28. |
| N990 | Carbon black, obtained under the trade designation "N990" from Cancarb, Medicine Hat, Alberta, Canada |

TABLE 1-continued

| Abbreviation | Description and Source |
|---|---|
| Ca(OH)$_2$ | An acid acceptor. Calcium hydroxide obtained under the trade designation "HALLSTAR CALCIUM HYDROXIDE HP-XL" from The Hallstar Company, Chicago, Illinois, USA |
| MgO | An acid acceptor. Magnesium oxide powder obtained under the trade designation "ELASTOMAG 170" from Akrochem Corp, Akron, OH, USA |
| BTPPCl | Benzyl triphenyl phosphonium chloride obtained from Alfa Aesar, Haverhill, MA, USA |
| C$_4$F$_9$SO$_2$NMe | C$_4$F$_9$SO$_2$NH—CH$_3$, CAS number 68298-12-4, obtained from Apollo Scientific Fluorine Chemicals |

Test Methods

Cure Rheology

Cure rheology tests were carried out using uncured, compounded samples using a rheometer (PPA 2000 by Alpha technologies, Akron, OH), in accordance with ASTM D 5289-93A at 177° C., no pre-heat, 12 minute elapsed time, and a 0.5 degree arc. Both the minimum torque ($M_L$) and highest torque attained during a specified period of time when no plateau or maximum torque ($M_H$) was obtained were measured. Also reported were the time for the torque to reach a value equal to $M_L+0.5(M_H-M_L)$, (t'50), and the time for the torque to reach $M_L+0.9(M_H-M_L)$, (t'90). Results are reported in Table 3.

Physical Properties

Tensile, elongation, and modulus data were gathered from both press and post cured samples cut at room temperature to Die D specifications in accordance with ASTM 412-06A.

Molded O-rings and Compression Set

O-rings (214, AMS AS568) were molded at 177° C. for 10 minutes at 400 kPa. The press cured O-rings were post cured at 250° C. for 16 hours. The post cured O-rings were tested for compression set for 70 hours at 200° C. in accordance with ASTM D 395-03 Method B and ASTM D1414-94 with a 25% deflection. Results are reported as percentages.

Comparative Example a (Comp. Ex. A): Reaction of Perfluoropropyl Allyl Ether, CF$_3$CF$_2$CF$_2$OCF$_2$CF═CF$_2$ with Ammonia A 600 milliliter (mL) Parr reactor (Parr Instrument Company, Moline, IL, USA) was evacuated to 25 millimeter (mm) vacuum. The vacuum evacuated reactor was then charged with 50 grams (0.16 mol) C$_3$F$_7$OCF$_2$CF═CF$_2$ (MA3, made as described in U.S. Pat. No. 5,891,965 as PPAE-2) along with 150 grams of methyl tert-butyl ether. The reactor was stirred and cooled to −2° C. The addition of 13 grams (0.77 mol) ammonia was then metered into the reactor over thirty minutes. No temperature increase was noted during the ammonia addition. The reactor was then warmed to 25° C. and the mixture was drained. The brown-colored slurry was washed with 250 grams deionized water and the top brown-colored organic phase was distilled to recover solvent with unreacted MA3. The product remaining after distillation of MA3, was analyzed. The product contained CF$_3$CF$_2$CONH$_2$ amide by-product and no amidine product was identified by FTIR and NMR.

Example 1: Preparation of (HOCH$_2$(CF$_2$)$_5$OCFH)$_3$—C$_3$N$_3$, (1H-MV5CH2OH)$_3$-Triazine HOCH$_2$C$_5$F$_{10}$OCF═CF$_2$ was prepared as follows, perfluoroadipoyl fluoride was coupled with hexafluoropropylene oxide as described in U.S. Pat. Publication 2004/0116742 found in Example 3 to isolate FCO(CF$_2$)$_5$OCF(CF$_3$)COF (boiling point of 135° C.). To a 2 Liter (L)3-neck round bottom flask equipped with a mechanical stirrer, thermocouple, and condenser, 143 grams (1.35 mol) of sodium carbonate and 400 grams diglyme was added and stirred while heating to 82° C. A charge of 250 grams (0.54 mol) FCO(CF$_2$)$_5$OCF(CF$_3$)COF was added over one hour and stirred for an hour. The temperature was increased to 145° C. and held for two hours. The reaction mixture was the cooled to 38° C. and 365 grams of 60% sulfuric acid was added at a rate to keep the temperature below 60° C. After acid addition, the mixture phase split to give the product in the top phase. The top phase was washed twice with 264 grams of 24% sulfuric acid to give the CF$_2$═CFO(CF$_2$)$_5$CO$_2$H product in the lower phase. Esterification to the methyl ester was done by adding 116 grams methanol followed by 64 grams of concentrated sulfuric acid to CF$_2$═CFO(CF$_2$)$_5$CO$_2$H and heating to 82° C. for 20 hours. The solution was then cooled to 25° C. and 200 grams of distilled water was added to give the fluorochemical product in the lower phase. Vacuum distillation gave 110 grams (0.27 mol) CF$_2$═CFO(CF$_2$)$_5$CO$_2$CH$_3$ boiling at 108° C. at 25 mm for a 50% yield. To a 1 L 3-neck round bottom flask equipped with a mechanical stirrer, thermocouple, and condenser, 7.3 grams (0.19 mol) of NaBH$_4$ and 165 g isopropanol was added and stirred while cooling to 5° C. A charge of 110 grams (0.27 mol) CF$_2$═CFO(CF$_2$)$_5$CO$_2$CH$_3$ was added over one hour and stirred for an hour at 5° C. Dropwise, 205 grams of 14% sulfuric acid was then added over one hour at 5° C. The solution was then stirred at 25° C. for 20 hours and subsequently charged with a mixture of 33 grams sodium chloride in 110 grams distilled water to get the product in the top phase with isopropanol. Atmospheric distillation of isopropanol followed by vacuum fraction gave 96 grams (0.25 mol) CF$_2$═CFO(CF$_2$)$_5$CH$_2$OH (MV5-CH2OH with a boiling point of 68° C. at 13 mm vacuum for a 94% yield and 97.5% purity based on GC).

A 600 mL Parr reactor was evacuated to 25 mm vacuum. The vacuum evacuated reactor was then charged with 62 grams (0.16 mol) HOCH$_2$(CF$_2$)$_5$OCF═CF$_2$ along with 150 grams of methyl tert-butyl ether. The reactor was then stirred and cooled to −1° C. The addition of 11 grams (0.65 mol) ammonia was metered into the reactor over thirty minutes which caused the temperature to rise to 4° C. The reactor was then warmed to 25° C. and excess ammonia was vented. The mixture was then stirred at 25° C. for 20 hours. The resulting slurry was filtered through a glass-fritted funnel and the solvent was removed by atmospheric distillation. After the solvent was removed, the oil bath was set to 150° C. and held at that temperature for thirty minutes. Off-gassing was monitored through a bubbler. Heating was then stopped and the flask was cooled to 25° C. FTIR analysis showed a strong peak at 1564 cm$^{-1}$ for the triazine formation. Vacuum distillation yielded 27 grams (0.03 mol) of (HOCH$_2$(CF$_2$)$_5$OCFH)$_3$—C$_3$N$_3$, (1H-MV5CH2OH)3-Triazine with boiling point of 260° C. at 11 mm for a 46% yield. $^1$H- and $^{19}$F-NMR confirmed the desired compound. GC/MS gave 87% purity.

Example 2(Ex. 2) and Example 3(Ex. 3) were 200 gram polymer batches that were compounded on a two-roll mill using the amounts listed in Table 2. These curable fluoropolymer compositions were then tested for their cure rheology and physical properties after press cure, physical properties after press cure and post cure, and their compression set. The results are shown in Table 3 below.

TABLE 2

| Material | Ex. 2 | Ex. 3 |
|---|---|---|
| Fluoropolymer A | 100 | 100 |
| N990 | 30 | 30 |
| Ca(OH)$_2$ | 6 | 6 |
| MgO | 3 | 3 |
| (1H-MV5CH2OH)3-triazine | 6.4 | 6.4 |
| BTPPCl | 1 | 1 |
| C$_4$F$_9$SO$_2$NMe | 0 | 1 |

TABLE 3

Physical Properties

|  | Ex. 2 | Ex. 3 |
|---|---|---|
| Cure rheology (177° C., 12 minutes) | | |
| M$_L$, Minimum Torque, dNm | 0.9 | 0.8 |
| M$_H$, Maximum Torque, dNm | 10.1 | 18.8 |
| t'50, Time to 50% cure - minutes | 0.8 | 0.5 |
| t'90, Time to 90% cure - minutes | 6.1 | 1.0 |
| Tensile Properties (Press Cure at 177° C. (350° F.), 10 minutes) | | |
| Tensile, MPa | 8.2 | 9.7 |
| Elongation at break, % | 407 | 244 |
| 50% Modulus, MPa | 1.9 | 2.6 |
| 100% Modulus, MPa | 2.9 | 4.8 |
| Hardness, Shore A | 71 | 74 |
| Tensile Properties (Post Cure at 250° C. (482° F.), 16 hours) | | |
| Tensile, MPa | 11.3 | 14.2 |
| Elongation at break, % | 230 | 146 |
| 50% Modulus, MPa | 2.8 | 4.3 |
| 100% Modulus, MPa | 5.0 | 9.5 |
| Hardness, Shore A | 78 | 80 |
| Compression Set 70 hours at 200° C., 25% deflection | | |
| Post cure | 44 | 41 |

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A curable composition comprising (a) an amorphous fluorinated polymer capable of being dehydrofluorinated, and (b) a compound of Formula (I)

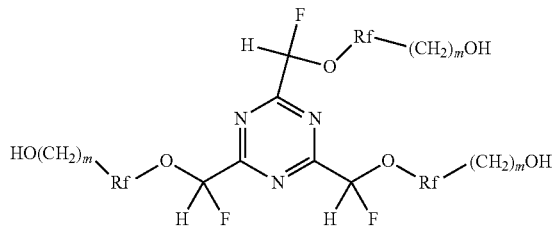

wherein each Rf is independently selected from a perfluorinated divalent group comprising 2 to 12 carbon atoms; and m is an integer independently selected from 1 to 3.

2. The curable composition of claim 1, wherein the molecular weight of compound of Formula (I) is less than 1500 grams/mole.

3. The curable composition of claim 1, wherein Rf is —(CF$_2$)$_n$—, where n is an integer from 2-8.

4. The curable composition of claim 1, wherein Rf comprises
—(CF$_2$)$_p$—O—(CF$_2$)$_q$, —(OCF$_2$CF$_2$)$_q$—, —(OCF$_2$CF(CF$_3$))$_p$— and/or —(CF$_2$CF(CF$_3$))$_p$—O—(CF$_2$)$_q$—, wherein p is an integer of 1-11 and q is an integer from 1-11, such that the sum of p+q is 2-12.

5. The curable composition of claim 1, wherein m is 1.

6. The curable composition of claim 1, wherein the compound according to Formula I is at least one of the following: [HOCH$_2$(CF$_2$)$_2$OCFH]$_3$—C$_3$N$_3$, [HO(CH$_2$)$_2$(CF$_2$)$_2$OCFH]$_3$—C$_3$N$_3$, [HO(CH$_2$)$_3$(CF$_2$)$_2$OCFH]$_3$—C$_3$N$_3$, [HO(CH$_2$)(CF$_2$)$_3$OCFH]$_3$—C$_3$N$_3$, [HO(CH$_2$)(CF$_2$)$_4$OCFH]$_3$—C$_3$N$_3$, [HO(CH$_2$)(CF$_2$)$_5$OCFH]$_3$—C$_3$N$_3$, [HO(CH$_2$)(CF$_2$)$_6$OCFH]$_3$—C$_3$N$_3$, [HO(CH$_2$)(CF$_2$)$_6$OCFH]$_2$—C$_3$N$_3$—[CHFO(CF$_2$)$_2$(CH$_2$)OH], [HO(CH$_2$)(CF(CF$_3$)O(CF$_2$)$_6$OCFH]$_2$—C$_3$N$_3$—[CHFO(CF$_2$)$_2$OCF(CF$_3$)CH$_2$OH], [HOCH$_2$CH$_2$CF(CF$_3$)O(CF$_2$)$_2$OCFH]$_3$—C$_3$N$_3$, [HOCH$_2$CF(CF$_3$)O(CF$_2$)$_2$OCFH]$_3$—C$_3$N$_3$, [HOCH$_2$(CF$_2$)$_3$OCF(CF$_3$) CF$_2$OCFH]$_3$—C$_3$N$_3$, [HOCH$_2$CH$_2$(CF$_2$)$_4$OCFH]$_3$—C$_3$N$_3$, [HOCH$_2$(CF$_2$)$_2$OCF(CF$_3$) CF$_2$OCFH]$_3$—C$_3$N$_3$, [HOCH$_2$CH$_2$(CF$_2$)$_2$OCF$_2$CF(CF$_3$) OCFH]$_3$—C$_3$N$_3$, and [HOCH$_2$(CF$_2$)$_5$OCF(CF$_3$) CF$_2$OCFH]$_3$—C$_3$N$_3$, where C$_3$N$_3$ represents the triazine ring.

7. The curable composition of claim 1, comprising at least 0.1 part by weight of the compound of Formula (I) to 100 parts by weight of the amorphous fluorinated polymer capable of being dehydrofluorinated.

8. The curable composition of claim 1, wherein the amorphous fluorinated polymer capable of being dehydrofluorinated comprises at least one of (i) vinylidene fluoride, tetrafluoroethylene, and propylene copolymer; (ii) vinylidene fluoride and hexafluoropropylene copolymer; (iii) hexafluoropropylene, tetrafluoroethylene, and vinylidene fluoride copolymer; (iv) hexafluoropropylene and vinylidene fluoride copolymer; (v) tetrafluoroethylene, propylene, and 3,3,3-trifluoropropene copolymer; (vi) tetrafluoroethylene, and propylene copolymer; and (vii) blends thereof.

9. The curable composition of claim 1, wherein the amorphous fluorinated polymer capable of being dehydrofluorinated comprises (i) at least one of vinylidene fluoride and tetrafluoroethylene, or (ii) a fluorinated comonomer having an acidic hydrogen atom.

10. The curable composition of claim 9, wherein the fluorinated comonomer having an acidic hydrogen atom comprises at least one of trifluoroethylene; vinyl fluoride; 3,3,3-trifluoropropene-1; pentafluoropropene; and 2,3,3,3-tetrafluoropropene.

11. The curable composition of claim 1, wherein the dehydrofluorinating agent is selected from an organo onium compound.

12. The curable composition of claim 11, wherein the organo onium compound is selected from at least one of quaternary ammonium hydroxides or salts, quaternary phosphonium hydroxides or salts, and ternary sulfonium hydroxides or salts.

13. The curable composition of claim 1, further comprising an organic or inorganic base.

14. The curable composition of claim 1, further comprising a sulfonamide.

15. A cured article derived from the curable composition of claim 1, optionally, wherein the cured article is an o-ring, a seal, a gasket, a hose or a sheet.

16. A molded article comprising the cured compositions of claim 15.

17. A method of making the compound according to Formula (I), the method comprising:

reacting a vinyl ether monomer according to Formula (II), with ammonia to form an amidine molecule; and heating the amidine molecule to form the compound according to Formula (I), where Formula (II) is

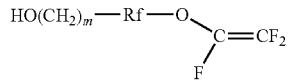

wherein Rf is a perfluorinated divalent group comprising 2 to 12 carbon atoms; and m is an integer independently selected from 1 to 3.

18. A method of preparing a shaped article comprising the steps of:

providing the curable composition of claim 1, heating said composition to a temperature sufficient to cure the curable composition; and recovering the shaped article.

19. A compound according to Formula (I)

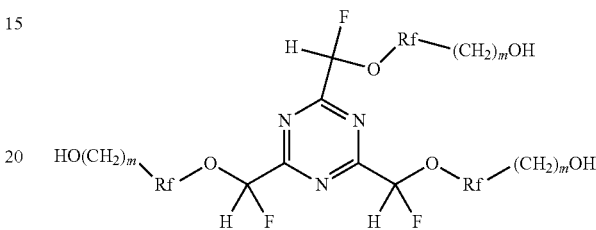

wherein each Rf is independently selected from a perfluorinated divalent group comprising 2 to 12 carbon atoms; and m is an integer independently selected from 1 to 3.

* * * * *